② United States Patent [19] | [11] 4,339,448
Dockner et al. | [45] Jul. 13, 1982

[54] IMIDAZOLE-COPPER COMPLEX COMPOUNDS AND FUNGICIDES CONTAINING THEM

[75] Inventors: Toni Dockner, Meckenheim; Anton Frank, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 87,556

[22] Filed: Oct. 22, 1979

[30] Foreign Application Priority Data

Nov. 2, 1978 [DE] Fed. Rep. of Germany ....... 2847441

[51] Int. Cl.[3] .......................... A01N 55/02; C07F 1/08

[52] U.S. Cl. ....................................... 424/245; 544/64; 544/225; 546/9; 546/12; 548/101; 548/109

[58] Field of Search ................ 548/101, 109; 424/245; 544/225, 64; 546/9, 12

[56] References Cited

U.S. PATENT DOCUMENTS

| | | | |
|---|---|---|---|
| 2,404,299 | 7/1946 | Kyrides | 548/335 |
| 2,881,176 | 4/1959 | Hogsett | 424/245 |
| 3,652,581 | 3/1972 | Spaenig et al. | 548/334 X |
| 3,677,978 | 7/1972 | Dowbenko et al. | 548/101 X |
| 3,843,667 | 10/1974 | Cupery | 548/101 |
| 4,005,083 | 1/1977 | Büchel et al. | 424/245 |
| 4,073,901 | 2/1978 | Büchel et al. | 424/245 |
| 4,073,921 | 2/1978 | Miller et al. | 424/273 R |
| 4,085,209 | 4/1978 | Miller et al. | 424/245 |
| 4,118,461 | 10/1978 | Miller et al. | 424/273 R |

OTHER PUBLICATIONS

Skapski et al., Chemical Abstracts, vol. 75, 41609x (1971).

Reedijk et al., Chemical Abstracts, vol. 78, 66389a (1973).

Goodgame et al., Chemical Abstracts, vol. 80, 8795k (1974).

Shirai et al., Chemical Abstracts, vol. 81, 121190t (1974).

Massacesi et al., Chemical Abstracts, vol. 82, 38097t (1975).

Mohapatra et al., Chemical Abstracts, vol. 87, 192962f (1977).

Reedijk, J. Inorg. Nucl. Chem., vol. 33, No. 1, pp. 179–188 (1971).

Farm Chemicals Handbook (1979), p. D70.

*Primary Examiner*—Donald G. Daus
*Assistant Examiner*—Diana G. Rivers
*Attorney, Agent, or Firm*—Keil & Witherspoon

[57] ABSTRACT

New imidazole-copper complex compounds having a good fungicidal action, fungicides containing these compounds as active ingredients, processes for their manufacture, and their use for combating fungi.

5 Claims, No Drawings

IMIDAZOLE-COPPER COMPLEX COMPOUNDS AND FUNGICIDES CONTAINING THEM

The present invention relates to new and valuable imidazole-copper complex compounds having a good fungicidal action, fungicides containing these compounds as active ingredients, processes for their manufacture, and their use for combating fungi.

The use of copper oxychloride as a fungicide has been disclosed. However, its action is unsatisfactory.

We have found that imidazole-copper complex compounds of the formula

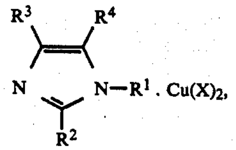

where $R^1$, $R^2$, $R^3$ and $R^4$ are identical or different and each denotes hydrogen or substituted or unsubstituted alkyl, aryl, imidazolyl or aralkyl, and $R^4$ may additionally denote nitro, and X denotes the anion of a mineral or lower fatty acid, have a better fungicidal action particularly on phytopathogenic fungi, e.g., *Plasmopara viticola* in grapes and Phytophthora infestans in tomatoes, than prior art fungicides.

Some of the new copper complex compounds are crystalline, others pasty or oily substances which are soluble in water, alcohols and various organic solvents.

The new compounds are produced by reaction of an imidazole of the formula

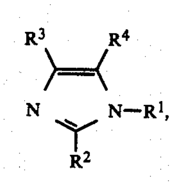

where $R^1$, $R^2$, $R^3$ and $R^4$ have the above meanings, with a neutral or basic copper salt of a mineral acid or lower fatty acid. It is preferred to use for the reaction copper(II) chloride or another copper salt of a mineral acid or lower fatty acid. For instance, the imidazole may be mixed with the copper salt, or a methanolic solution of the imidazole with, for example, copper chloride, after which the methanol is distilled off.

Examples of meanings for $R^1$ to $R^4$ in the general formula of the new imidazole-copper complex compounds are as follows:

$R^1$: hydrogen, methyl, ethyl, propyl, hexyl, heptyl, octyl, decyl, undecyl, dodecyl, tridecyl, tetradecyl, hexadecyl, octadecyl, phenyl, p-aminophenyl, benzyl, cyanobenzyl, phenylethyl, isobutylbenzyl, pyrrolidylethyl, morpholinoethyl, piperidinoethyl, dibutylaminoethyl and phenylbenzylaminoethyl;

$R^2$: hydrogen, methyl, ethyl, propyl, isopropyl, octyl, decyl, dodecyl, octadecyl, phenyl, methoxyphenyl, benzyl, indanyl, dimethylphenyl and butylphenyl;

$R^3$: hydrogen, methyl, ethyl, propyl, isopropyl, butyl, isobutyl, phenyl and cyclohexyl;

$R^4$: hydrogen, nitro, cyano, carboxy, hydroxymethyl and hydroxyethyl.

Examples of mineral acids are hydrochloric acid, hydrobromic acid, sulfuric acid, nitric acid, phosphoric acid and sulfonic acids, e.g., p-toluenesulfonic acid and dodecylbenzenesulfonic acid. Examples of lower fatty acids are formic acid, acetic acid, propionic acid, oxalic acid, tartaric acid, ascorbic acid and citric acid.

The production of the imidazole-copper complex compounds by reaction of an imidazole with a copper salt may be carried out for example without solvents or in the presence of a solvent, at from −10° to +170° C.

Examples of solvents are water, methanol, ethanol, isopropanol and dimethylformamide. A liquid imidazole itself may also be used as solvent for the reaction. The starting materials are employed in stoichiometric amounts or one of the starting materials is employed in excess. As the copper salts are readily accessible, they are preferably used in an excess, for example an up to tenfold excess over the stoichiometric amount. The reactions take place at atmospheric pressure, but may of course—although this is not necessary—also be carried out at sub- or superatmospheric pressure. The reaction therefore preferably takes place at atmospheric pressure, with methanol as solvent, with a slight excess (up to 10%) of copper chloride, and at 20° C. The following example illustrates the reaction.

EXAMPLE 1

Manufacture of 1-dodecylimidazole-$CuCl_2$

While cooling, 59 parts (by weight) of 1-dodecylimidazole is added to a solution of 42.5 parts of $CuCl_2.2H_2O$ in 200 parts of methanol. The mixture is evaporated in vacuo. There is obtained 93 parts of a dark, syrupy residue which contains 16.0% of Cu (active ingredient 1).

EXAMPLE 2

In accordance with Example 1, the following compounds are obtained by reaction of various imidazoles with $CuCl_2$.

| Active ingredient no. | | m.p. |
|---|---|---|
| 2 | Imidazole . $CuCl_2$ (yellowish green crystals) | 198° C. |
| 3 | 1-Hexylimidazole . $CuCl_2$ (dark oil) | |
| 4 | 1-(2-pyrrolidylethyl)-imidazole . $CuCl_2$ | 119° C. |
| 5 | 1-(2-morpholinoethyl)-imidazole . $CuCl_2$ | 108° C. |
| 6 | 1-(2-piperidinoethyl)-imidazole . $CuCl_2$ | 106° C. |
| 7 | 1-Heptylimidazole . $CuCl_2$ (dark oil) | |
| 8 | 1-(2-Cyanobenzyl)-imidazole . $CuCl_2$ | 209–210° C. |
| 9 | 1-(1-Phenyl-2-chloroethyl)-imidazole . $CuCl_2$ | 163–64° C. |
| 10 | 1-Octylimidazole . $CuCl_2$ (dark oil) | |
| 11 | 1-(2-Ethylhexyl)-imidazole . $CuCl_2$ (paste) | |
| 12 | 1-Decylimidazole . $CuCl_2$ (dark oil) | |
| 13 | 1-(2-Dibutylaminoethyl)-imidazole . $CuCl_2$ | 128° C. |

-continued

| Active ingredient no. | | m.p. |
|---|---|---|
| 14 | 1-(p-Isobutylbenzyl)-imidazole . $CuCl_2$ | 64–65° C. |
| 15 | 1-Undecylimidazole . $CuCl_2$ (oil) | |
| 16 | 1-Isotridecylimidazole . $CuCl_2$ (oil) | |
| 17 | 1-Tetradecylimidazole . $CuCl_2$ | 74° C. |
| 18 | 1-(2-N-Phenyl-N-benzylaminoethyl)-imidazole . $CuCl_2$ | 60° C. |
| 19 | 1-Hexadecylimidazole . $CuCl_2$ | 68–70° C. |
| 20 | 1-Octadecylimidazole . $CuCl_2$ | 54–55° C. |
| 21 | 1-(p-Aminophenyl)-imidazole . $CuCl_2$ | 208° C. |
| 22 | 2-Heptylimidazole . $CuCl_2$ | 115° C. |
| 23 | 2-(2,6-Dimethylhepten-6-yl)-imidazole . $CuCl_2$ (oil) | |
| 24 | 2-(1-Piperonylpropyl)-imidazole . $CuCl_2$ (oil) | |
| 25 | 2-(1-p-Isobutylphenylethyl)-imidazole . $CuCl_2$ (oil) | |
| 26 | 2-Dodecylimidazole . $CuCl_2$ (paste) | |
| 27 | 2-Octadecylimidazole . $CuCl_2$ (paste) | |
| 28 | 2,2'-Diimidazolyl . $CuCl_2$ | 360° C. |
| 29 | 2-Phenylimidazole . $CuCl_2$ | 170° C. |
| 30 | 2-(2-Methoxyphenyl)-imidazole . $CuCl_2$ | 107° C. |
| 31 | 1,2-Dimethylimidazole . $CuCl_2$ | 225–226° C. |
| 32 | 1-Methyl-2-ethylimidazole . $CuCl_2$ | 237–239° C. |
| 33 | 1-(2-Dimethylaminoethyl)-2-methylimidazole . $CuCl_2$ | 116° C. |
| 34 | 1-(2-Piperazinoethyl)-2-methylimidazole . $CuCl_2$ | 135–139° C. |
| 35 | 1-(2-Pyrrolidinoethyl)-2-methylimidazole . $CuCl_2$ | 120–127° C. |
| 36 | 1-Methyl-2-(2-pyrrolidinoethyl)-imidazole . $CuCl_2$ | 134–135° C. |
| 37 | 1-(3,3-dimethylbutyl)-2-methylimidazole . $CuCl_2$ | 240° C. |
| 38 | 1-Methyl-2-octylimidazole . $CuCl_2$ (paste) | |
| 39 | 1-Decyl-2-methylimidazole . $CuCl_2$ | 130–132° C. |
| 40 | 1-(1-Methyl-2-hydroxyethyl)-2-indanylimidazole . $CuCl_2$ | 79–80° C. |
| 41 | 1-Dodecyl-2-methylimidazole . $CuCl_2$ | 154–155° C. |
| 42 | 1-Phenyl-2-(3,4-dimethylphenyl)-imidazole . $CuCl_2$ | 180–181° C. |
| 43 | 1-Dodecyl-2-(1,1-dimethyl-2-acetoxyethyl)-imidazole . $CuCl_2$ (oil) | |
| 44 | 1-(2-N-Phenyl-N-benzylaminoethyl)-2-phenyl-imidazole . $CuCl_2$ | 69–70° C. |
| 45 | 1-Dodecyl-2-(1-p-tert-butylphenylethyl)-imidazole . $CuCl_2$ | 114–116° C. |
| 46 | 2-Methyl-4(5)-nitroimidazole . $CuCl_2$ | 238° C. |
| 47 | 1,2-Dimethyl-5-nitroimidazole . $CuCl_2$ | 204° C. |
| 48 | 1-(2-Aminoethyl)-2-methyl-5-nitroimidazole . $CuCl_2$ | 90–91° C. |
| 49 | 1-Methyl-2-isopropyl-5-nitroimidazole . $CuCl_2$ | 242° C. |
| 50 | 2,4(5)-Dimethyl-5(4)-propylimidazole . $CuCl_2$ (oil) | |
| 51 | 2-Phenyl-4,5-dimethylimidazole . $CuCl_2$ | 161° C. |
| 52 | 2-(2-Hydroxyphenyl)4,5-dimethylimidazole . $CuCl_2$ (paste) | |
| 53 | 2-(2-Phenylpropyl)-4(5)-methyl-5(4)-isobutyl-imidazole . $CuCl_2$ | 60° C. |
| 54 | 1-Dodecyl-4(5)-cyano-5(4)-carboxylimidazole . $CuCl_2$ | 214° C. |
| 55 | 1,2,4-Trimethyl-5-nitroimidazole . $CuCl_2$ (paste) | |
| 56 | 1,4-Dimethyl-2-hydroxymethyl-5-nitroimidazole . $CuCl_2$ | 193° C. |
| 57 | 1,2,4,5-Tetramethylimidazole . $CuCl_2$ (paste) | |
| 58 | 1-(2-Dimethylaminoethyl)-2,4,5-trimethylimidazole . $CuCl_2$ (oil) | |
| 59 | 1-(2-Pyrrolidylethyl)-2,4,5-trimethylimidazole . $CuCl_2$ | 105° C. |
| 60 | 1-Dodecyl-2,4,5-trimethylimidazole . $CuCl_2$ (oil) | |
| 61 | 1-Dodecyl-2,4-diethyl-5-methylimidazole . $CuCl_2$ (oil) | |
| 62 | 1-Dodecyl-2-phenyl-4,5-dimethylimidazole . $CuCl_2$ (oil) | |
| 63 | 1-Dodecyl-2-methyl-4-ethyl-5-cyclohexylimidazole . $CuCl_2$ (oil) | |
| 64 | 1-Dodecyl-2-methyl-4-ethyl-5-benzylimidazole . $CuCl_2$ (oil) | |

EXAMPLE 3

118 parts of 1-dodecylimidazole and 80 parts of anhydrous copper sulfate are heated to 100° C. in a stirred flask; in a slightly exothermic reaction, a homogeneous melt is formed which soon solidifies. There is obtained 168 parts of a complex of 1-dodecylimidazole and $CuSO_4$ having a melting point of 216°–218° C. (active ingredient 65).

EXAMPLE 4

104 parts of 1-decylimidazole and 100 parts of copper(II) acetate monohydrate are intimately mixed at 140° C. After cooling, there is obtained 195 parts of a pale blue, pasty mass of a complex of 1-decylimidazole and copper acetate (active ingredient 66).

The active ingredients according to the invention have a strong fungicidal action on phytopathogenic fungi, especially from the Phycomycetes class. The new compounds are therefore suitable for instance for combating *Phytophthora infestans* in tomatoes and potatoes, *Phytophthora parasitica* in strawberries, *Pseudoperonospora humuli* in hops, *Peronospora tabacina* in tobacco, and *Plasmopara viticola* in grapes. The fungicidal agents contain from 0.1 to 95% (by weight) of active ingredient, preferably from 0.5 to 90%. The application rates depend on the effect desired, and are from 0.1 to 5 kg of active ingredient per hectare.

The new compounds may also be used to combat fungi which cause seedling diseases, e.g., Pythium species.

Some of the compounds also have a bactericidal and algicidal action.

The active ingredients of the invention can be converted into the conventional formulations, e.g. solutions, emulsions, suspensions, dusts, powders, pastes and granules. The form of application depends entirely on the purpose for which the agent is to be used; at all events, it should ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.g. petroleum fractions, alcohols, e.g. methanol and butanol, amines, e.g. ethanolamine and dimethylformamide, and water; carriers for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The formulations, and the ready-to-use preparations obtained therefrom, e.g., solutions, emulsions, suspensions, powders, dusts, pastes or granules, are applied in the conventional manner, e.g. by spraying, atomizing, dusting, treating seed, or watering.

The active ingredients according to the invention may be mixed and applied with other active ingredients, e.g. herbicides, insecticides, growth regulators and other fungicides or may be mixed with fertilizers and applied together with these. Mixture with other fungicides often broadens the spectrum of fungicidal action. Synergistic effects also occur with a number of these fungicidal mixtures, i.e., the fungicidal action of the combination product is greater than that of the individual components added together.

The following list of fungicides with which the compounds according to the invention may be combined is intended to illustrate and not restrict the combination possibilities. Examples of fungicides which can be combined with the compounds of the invention are: dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and zinc N,N'-propylene-bis-dithiocarbamate, and the ammonia complex of zinc N,N'-propylene-bis-dithiocarbamate and N,N'-polypropylene-bis-(thiocarbamoyl)-disulfide; nitro derivatives, e.g. dinitro-(1-methylheptyl)-phenyl crotonate, 2-sec.-butyl-4,6-dinitrophenyl-3,3-dimethylacrylate and 2-sec.-butyl-4,6-dinitrophenyl isopropyl carbonate; heterocyclic compounds, e.g. N-trichloromethylthiotetrahydrophthalimide, N-trichloromehylthio-phthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenylhydrazono)-3-methyl-5-isoxazolone, pyridine-2-thio-1-oxide, 8-hydroxyquinoline and its copper salt, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2,5-dimethylfuran-3-carboxylic acid cyclohexylamide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, and 2,6-dimethyl-N-cyclododecyl-morpholine and its salts.

The following examples demonstrate the fungicidal action.

EXAMPLE 5

Fungicidal action on *Phytophthora infestans* in tomatoes

Leaves of tomato plants of the "Professor Rudloff" variety are sprayed with aqueous dispersions containing (dry basis) 80% (wt%) of active ingredient and 20% of sodium lignin sulfonate. 0.2 and 0.1% (dry basis) spray liquors are used. After the sprayed-on layer has dried, the leaves are infected with a zoospore suspension of *Phytophthora infestans*. The plants are then placed for 5 days in a steam-saturated (moist) chamber kept at 16° to 18° C. After this period, the disease has spread on the untreated control plants to such an extent that the fungicidal action of the compounds can be assessed.

| Active ingredient | Leaf attack after spraying with liquor containing active ingredient in amounts of | |
|---|---|---|
| | 0.2% | 0.1% |
| 1 | 0 | 0 |
| 4 | 0 | 0 |
| 5 | 0 | 0 |
| 7 | 0 | 0 |
| 8 | 0 | 0 |
| 10 | 0 | 0 |
| 11 | 0 | 0 |
| 12 | 0 | 0 |
| 13 | 0 | 0 |
| 14 | 0 | 0 |
| 18 | 0 | 0 |
| 20 | 0 | 0 |
| 22 | 0 | 0 |
| 32 | 0 | 0 |
| 33 | 0 | 0 |
| 38 | 0 | 0 |
| 39 | 0 | 0 |
| 42 | 0 | 0 |
| 43 | 0 | 0 |
| 59 | 0 | 0 |
| 60 | 0 | 0 |
| 62 | 0 | 0 |
| 63 | 0 | 0 |
| 66 | 0 | 0 |

-continued

| Active ingredient | Leaf attack after spraying with liquor containing active ingredient in amounts of | |
|---|---|---|
| | 0.2% | 0.1% |
| Copper oxychloride (prior art) | 1 | 2 |
| Control (untreated) | 5 | |

0 = no attack, graduated down to 5 = total attack (control)

EXAMPLE 6

Fungicidal action on *Plasmopara viticola* in grapes

Leaves of potted vines of the Müller-Thurgau variety are sprayed with aqueous suspensions containing (dry basis) 80% (wt%) of the active ingredient and 20% of sodium lignin sulfonate. 0.1, 0.05 and 0.025% (dry basis) spray liquors are used. After the sprayed-on liquor has dried, the leaves are infected with a zoospore suspension of *Plasmopara viticola.* The plants are first placed for 16 hours in a steam-saturated (moist) chamber at 20° C., and then in a greenhouse for 8 days at from 20° to 30° C. To accelerate and intensify the sporangiophore discharge, the plants are then again placed in the moist chamber for 16 hours. Leaf attack is then assessed as follows: 0=no damage, graduated down to 5=total attack (control).

| Active ingredient | Leaf attack after spraying with liquor containing active ingredients in amounts of | | |
|---|---|---|---|
| | 0.1% | 0.05% | 0.025% |
| 10 | 0 | 0 | 0 |
| 14 | 0 | 0 | 1 |
| 32 | 0 | 0 | 0 |
| 38 | 0 | 0 | 0 |
| 39 | 0 | 0 | 2 |
| 42 | 0 | 0 | 0 |
| 43 | 0 | 0 | 2 |
| Copper oxychloride (prior art) | 2 | 3 | 4 |
| Control (untreated) | | 5 | |

EXAMPLE 7

90 parts by weight of compound 1 is mixed with 10 parts by weight of N-methyl-α-pyrrolidone. A mixture is obtained which is suitable for application in the form of very fine drops.

EXAMPLE 8

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 10

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 12

3 parts by weight of compound 3 is intimately mixed with 97 parts by weight of particulate kaolin. A dust is obtained containing 3% by weight of the active ingredient.

EXAMPLE 13

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 14

40 parts by weight of compound 1 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 15

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. An imidazole-copper complex compound of the formula

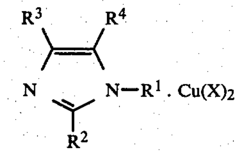

wherein $R^1$ is hexyl, heptyl, octyl, decyl, undecyl, dodecyl, tridecyl, tetradecyl, hexadecyl, octadecyl, p-aminophenyl, cyanobenzyl, phenylethyl, isobutylbenzyl, pyrrolidylethyl, morpholinoethyl, piperidinoethyl, di-butylaminoethyl or phenylbenzylaminoethyl;

$R^2$ is hydrogen, methyl, ethyl, propyl, isopropyl, octyl, decyl, dodecyl, octadecyl, phenyl, methoxyphenyl, benzyl, indanyl, di-methylphenyl or butylphenyl;

$R^3$ is hydrogen, methyl, ethyl, propyl, isopropyl, butyl, isobutyl, phenyl or cyclohexyl;

$R^4$ is hydrogen, nitro, cyano, carboxy, hydroxymethyl or hydroxyethyl; and

X is the anion of a mineral acid or a lower fatty acid.

2. A $CuCl_2$ salt of an imidazole selected from the group consisting of 1-(1-phenyl-2-chloroethyl)-imidazole; 1-(2-ethylhexyl)-imidazole; 2-(2,6-dimethyl-hepten-6-yl)-imidazole; 2-heptylimidazole; 2-(1-piperonylpropyl)-imidazole; 2-(1-p-isobutylphenylethyl)-imidazole; 2,2'-diimidazole; 2-(2-methoxyphenyl)-imidazole; 1-(2-dimethylaminoethyl)-2-methylimidazole; 1-(2-piperazinoethyl)-2-methylimidazole; 1-methyl-2-(2-pyrrolidinoethyl)-imidazole; 1-(3,3-dimethylbutyl)-2-methylimidazole; 1-methyl-2-octylimidazole; 1-(1-methyl-2-hydroxyethyl)-2-indanylimidazole; 1-phenyl-2-(3,4-dimethylphenyl)-imidazole; 1-dodecyl-2-(1,1-dimethyl-2-acetoxyethyl)-imidazole; 1-dodecyl-2(1-p-tert-butylphenylethyl)-imidazole; 2-methyl-4(5)-nitroimidazole; 1,2-dimethyl-5-nitroimidazole; 1-(2-aminoethyl)-2-methyl-5-nitroimidazole; 1-methyl-2-isopropyl-5-nitroimidazole; 2,4(5)-dimethyl-5(4)-propylimidazole; 2-phenyl-4,5-dimethylimidazole; 2-(2-hydroxyphenyl)-4,5-dimethylimidazole; 2-(2-phenylpropyl)-4(5)-methyl-5(4)-isobutylimidazole; 1-dodecyl-4(5)-cyano-5(4)-carboxylimidazole; 1,2,4-trimethyl-5-nitroimidazole; 1,4-dimethyl-2-hydroxymethyl-5-nitroimidazole; 1,2,4,5-tetramethylimidazole; 1-(2-dimethylaminoethyl)-2,4,5-trimethylimidazole; 1-(2-pyrrolidylethyl)-2,4,5-trimethylimidazole; 1-dodecyl-2,4,5-trimethylimidazole; 1-dodecyl-2,4-diethyl-5-methylimidazole; 1-dodecyl-2-phenyl-4,5-dimethylimidazole; 1-dodecyl-2-methyl-4-ethyl-5-cyclohexylimidazole; and 1-dodecyl-2-methyl-4-ethyl-5-benzylimidazole.

3. An imidazole-copper complex compound selected from the group consisting of 1-octylimidazole-$CuCl_2$, 1-dodecylimidazole-$CuCl_2$ and 1-tetradecylimidazole-$CuCl_2$.

4. A process for combatting phytopathogenic fungi, which comprises treating the fungi or the objects to be protected against fungus attack with a fungicidally effective amount of an imidazole-copper complex compound as set forth in claim 1.

5. A process for combatting phytopathogenic fungi, which comprises treating the fungi or the objects to be protected against fungus attack with a fungicidally effective amount of an imidazole-copper complex compound as set forth in claim 3 or 2.

* * * * *